United States Patent [19]
Michel

[11] Patent Number: 6,059,755
[45] Date of Patent: May 9, 2000

[54] INJECTION DEVICE FOR A LIQUID MEDICAMENT

[75] Inventor: Peter Michel, Burgdorf, Switzerland

[73] Assignee: Disetronic Licensing AG, Switzerland

[21] Appl. No.: 08/860,936

[22] PCT Filed: Nov. 9, 1995

[86] PCT No.: PCT/CH95/00261

§ 371 Date: Sep. 15, 1997

§ 102(e) Date: Sep. 15, 1997

[87] PCT Pub. No.: WO97/17095

PCT Pub. Date: May 15, 1997

[51] Int. Cl.$^7$ ...................................................... A61M 5/00
[52] U.S. Cl. ........................ 604/207; 604/187; 604/218; 604/232
[58] Field of Search ...................... 604/131, 134, 604/135, 181, 187, 207, 208, 209, 210, 211, 218, 220, 232, 234

[56] References Cited

U.S. PATENT DOCUMENTS 4,865,591  9/1989  Sams ........................................ 604/186
5,370,629  12/1994  Michel ..................................... 604/207
5,679,111  10/1997  Hjertman et al. ........................ 604/135

*Primary Examiner*—Wynn Wood Coggins
*Assistant Examiner*—LoAn H. Thanh
*Attorney, Agent, or Firm*—Dorsey & Whitney LLP

[57] ABSTRACT

The present invention provides an injection system including a disposable lower part and a reusable upper part wherein the lower part includes an ampoule holder for accommodating a container containing a liquid medicament and having an axially movable plug having a cross-section F for ejecting the liquid medicament from the container and a kinematic device for axially driving the plug forward by a number N of individual steps x, N being a natural number, and the reusable upper part includes a casing detachably connectable to the ampoule holder, and a dosing button for selecting the number N of individual steps x and for actuating the kinematic device of the lower part which thereby effects selectable ejection of a Volume V=NxF of the liquid medicament from the container.

8 Claims, 2 Drawing Sheets

INJECTION DEVICE FOR A LIQUID MEDICAMENT

BACKGROUND OF THE INVENTION

1. Field of the Invention

The invention relates to an injection device for receiving a liquid medicament injectable into a human or animal body by means of a needle, which device comprises the following parts: A) a disposable lower part comprising an ampoule holder for accommodating a container containing the liquid medicament, said container having an axially movable plug having a cross-section F for ejecting the liquid medicament from the container, a kinematic device for axially driving the plug forward by a number N of individual steps x, N being a natural number, B) a reusable upper part comprising a casing being detachably connectable to the ampoule holder of the lower part, dosing means for selecting the number N of individual steps x, ejection means for activating the kinematic device of the lower part which effects selectable ejection of a Volume V=NxF of the liquid medicament from the container.

2. Description of the Prior Art

Due to their specific form and analogy to a writing pen, such devices are generally referred to as "injection pens" or just "pens".

According to the prior art, there are essentially two different types of such injection pens.

Examples for devices according to the first group which are intended for one use only are described in detail in the documents EP-B 327 910, EP-A 496 141 and U.S. Pat. No. 5,295,976. In these devices, the ampoule which contains the liquid medicament is incorporated directly in the injection pen and delivered to the patient as a unit. Consequently, these devices are disposed of as a whole when exhausted which, owing to the more complicated parts of the pen which may, for example, also comprise a dosage and metering device, is rather costly. Devices of this group are therefore very expensive nor do they offer any solution for reusing single parts due to the different materials used therein.

Examples for devices of the second group which may be reused are described in detail in the documents DE-C 36 38 984, EP-A 498 737 and U.S. Pat. No. 4,883,472. In these devices, the exhausted ampoule may be replaced by a fresh one. However, the exchange procedure for the ampoule is rather complicated in these known devices. In order to insert a new ampoule into the device, the advance drive mechanism thereof must be returned to a defined starting position (for example by turning the plunger rod equipped with a thread). In order to be able to safely carry out this procedure, the patient must be instructed with due care. Another disadvantage resides in the risk of malfunctions of the dosage mechanism since said mechanism will soon be worn through frequent use.

SUMMARY OF THE INVENTION

It is the objective of the invention to offer a remedy. The invention is based on the objective to overcome the above-mentioned disadvantages of the prior art.

The invention solves the objective with an injection device for receiving a liquid medicament injectable into a human or animal body by means of a needle, which device comprises the following parts: A) a disposable lower part comprising an ampoule holder for accommodating a container containing the liquid medicament, said container having an axially movable plug having a cross-section F for ejecting the liquid medicament from the container, a kinematic device for axially driving the plug forward by a number N of individual steps x, N being a natural number, B) a reusable upper part comprising a casing being detachably connectable to the ampoule holder of the lower part, dosing means for selecting the number N of individual steps x, ejection means for activating the kinematic device of the lower part which effects selectable ejection of a Volume V=NxF of the liquid medicament from the container.

Consequently, the lower disposable part comprises those elements which are either exhausted during use or are less complicated and therefore less costly, such as plastic parts:
- the ampoule holder for receiving a container for the liquid medicament,
- the needle holder,
- the ratchet,
- the threaded screw nut,
- the plunger rod provided with a thread metal parts
- the spring (which is disposed around the plunger rod and pressed against the threaded screw nut to keep it in its axial position).

The upper reusable part comprises those elements which are not exhausted during use or which are complicated and/or costly, e.g.
- the rotatable dosage button,
- the coupling element for transferring the rotation of the dosage button to the threaded screw nut;
- a casing which is detachably attachable to the lower part,
- a counting device (not shown in the drawing) for recording the amount of the liquid medicament,
- a mechanical safety device.

The patient receives the device according to the invention in a two-part form which he can assemble before use. For this purpose he only has to click or screw the lower disposable part onto the upper reusable part. After exhaustion of the ampoule which contains the liquid medicament, the patient may throw away the entire lower part and attach a new lower part to the reusable upper part which comprises the valuable elements of the injection pen and may be reused over several years. Preferably, the lower part consists of recyclable materials only so that the burden on the environment can be kept minimal.

An important advantage of the device according to the invention consists in the possibility of using the upper part for the parallel administration of several different medicaments. Another advantage is the safe quantification of the medicament administration. Depending on the inner diameter of the ampoule and the thread pitch of the plunger rod, the amount of the ejected medicament may be defined exactly by the number of turns, one quarter of a full turn, for example, of a cam of the safety device preventing a reverse turn of the dosage button. The maximum dosage per injection is determined by the maximum lift of the dosage button. Therefore, the medicament dosage for a certain therapy is predetermined by the lower disposable part of the device according to the invention. Consequently, the upper part comprising the dosage unit is reduced to a simple adjustment and ejection mechanism which, if required, may be supplemented by a counting mechanism able to record the rotation movements (e.g. quarter turns).

Additional advantageous embodiments of the invention are characterised in the dependent claims.

BRIEF DESCRIPTION OF THE DRAWINGS

The invention and embodiments thereof will be illustrated in detail using the, in some part schematic, illustrations of an example, wherein.

DESCRIPTION OF THE PREFERRED EMBODIMENTS

Figure 1:
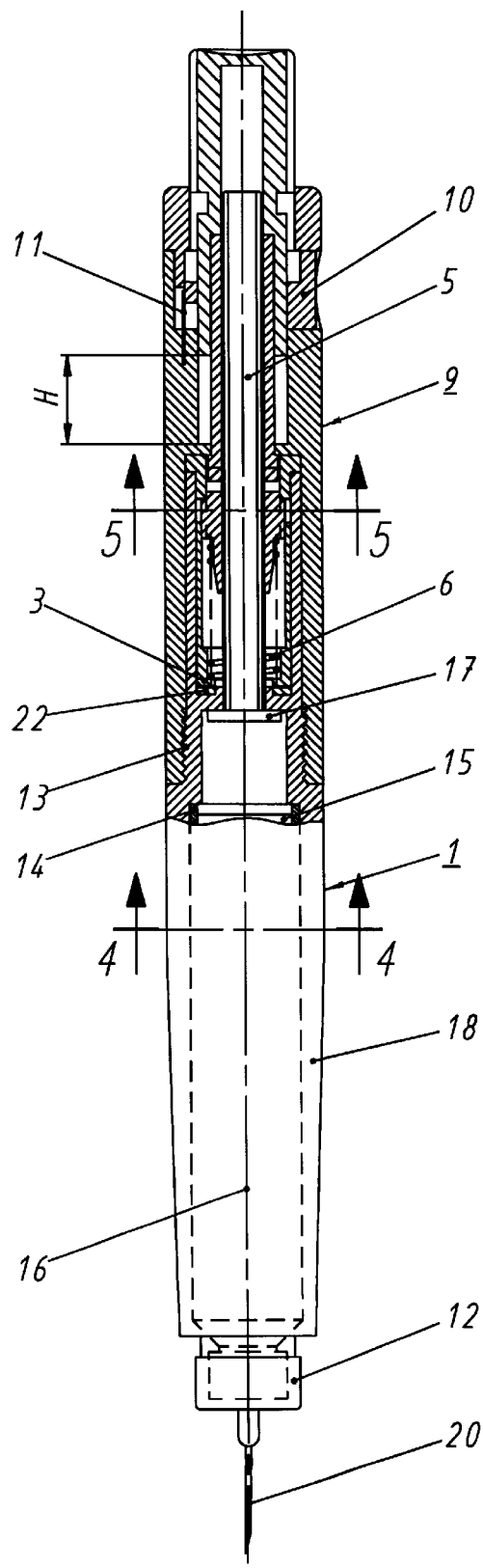
FIG. 1 shows a longitudinal section through a device according to the invention.

The injection device according to the invention shown in FIG. 1 is comprised of a lower part 1 and an upper part 9 which are coupled by means of a threaded connection 13 or a bayonet fastener. The lower part 1 is presented in FIG. 2 and the upper part in FIG. 3, both in the detached state.

Figure 5:
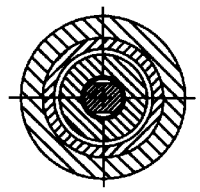
FIG. 5 is a sectional view of the device according to FIG. 1, taken along line 5—5 of FIG. 1.
Figure 2:
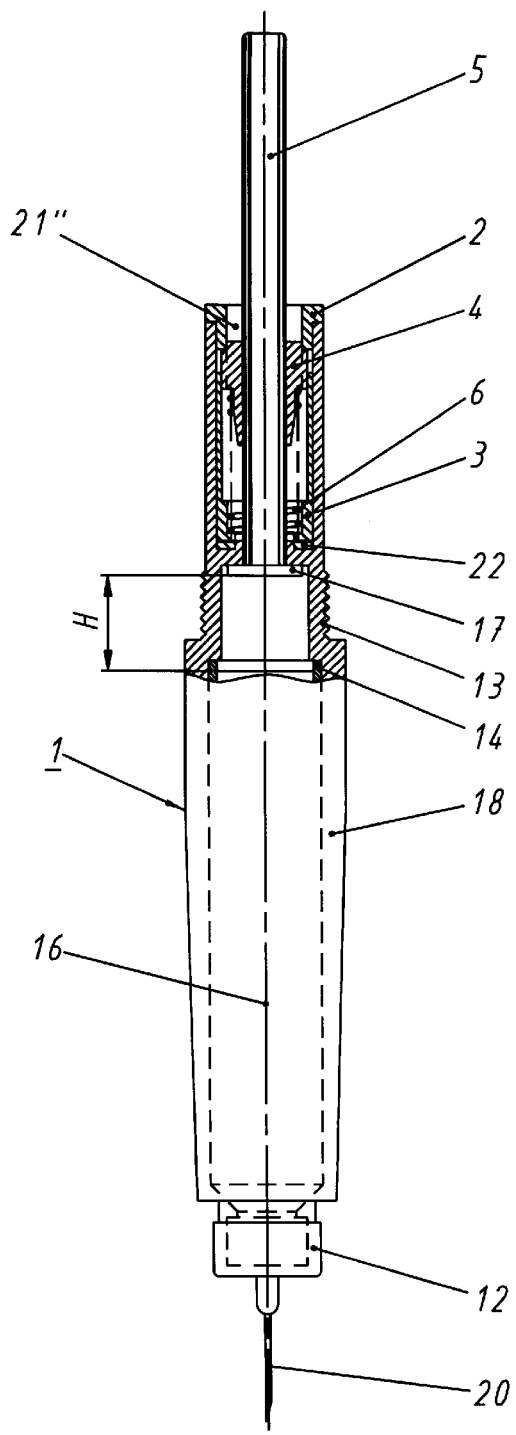
FIG. 2 shows a longitudinal section through the lower part of a device according to FIG. 1.

As shown in FIGS. 1 and 2, the cylindrical ampoule holder 18 of the lower part 1 comprises the container 14 for the liquid medicament. At the front end of the ampoule holder 18, the needle holder 12 with the needle 20 is screwed on. The container 14 which may consist of an ampoule is closed at its rear end by an axially shiftable plug 15. A non-rotatable, but axially shiftable plunger rod 5 is aligned in the longitudinal axis 16 of the injection device and can act on the plug 15 by means of its front plate 17. With reference to FIG. 5 the plunger rod 5 has an out-of-centre cross section so as to make it non-rotatable. The threaded screw nut 4 encircles the plunger rod 5, the two elements 4, 5 acting as a spindle/screw nut device. For this purpose, the screw nut 4 has an internal screw thread which corresponds to the thread of the plunger rod 5.

The screw nut 4 is connected with a tube 3 surrounding it which tube houses a spring 6 holding the screw nut 4 in its axial position. At its lower end, the spring 6 is secured by the tube 31 the diameter of which is reduced accordingly in this location. This construction guarantees that the spring 6 also turns when the screw nut 4 is rotated, since the screw nut 4 is non-rotatably, but axially shiftably connected with the tube 3.

At its upper end, the screw nut 4 is secured by a flange 2. A ratchet 22 which will be described in detail below is disposed at the lower end of the tube 3.

The hollow cylinder 7 which is connected to the button 8 in one piece, has a clutch 21' at its free end; accordingly, the screw nut 4 has a cooperating clutch 21" at its rear end. When the upper part 9 and the lower part 1 are combined, the clutches 21' and 21" engage.

Starting from the home position shown in FIG. 1, the function of the injection system will be described below. The user turns the button 8, thus transferring the rotation to the hollow cylinder 7 which is rotatably coupled to the screw nut 4 by means of the clutches 21' and 21". Since the screw nut 4 is kept in its axial position by the spring 6, an axial advance movement of the plunger rod 5 is effected by rotating the screw nut 4. The number of rotations N (e.g. quarter turns) of the button 8 is recorded by a suitable counting mechanism not shown in the drawing which operates either mechanically or electronically. At the same time, the safety device against reverse turns formed as a ratchet 22 (at the lower end of the tube 3) gives an acoustical or tactile signal, e.g. after each quarter turn of the button 8.

According to the number N of turns, the front plate 17 is moved closer towards the plug 15 by the relevant amount Nx, with x corresponding to the predeterminable number of discrete steps.

Figure 4:
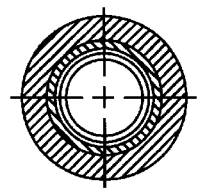
FIG. 4 is a sectional view of the device according to FIG. 1, taken along line 4—4 of FIG. 1.

After the above-described adjustment of the injection dosage, the button 8 is pushed down over its total predeterminable lift length H. When the plunger rod 5 has been moved forward by the amount Nx, the front plate 17 will first move forward by the length amount (H-Nx) until it touches the plug 15 and will then move on by the remaining amount Nx of the lift, discharging the volume V=NxF of the liquid medicament, with F corresponding to the inner cross-sectional area of the container 14. See FIG. 4 which is a sectional view of the present invention, including container 14 and illustrates generally that the container's cross-sectional area F may be derived in the conventional manner, i.e., by $\pi r^2$ or a function of the radius.

If the button 8 is not turned at all, no liquid medicament is ejected, because the front plate 17 only touches the plug 15 when it has travelled the entire lift length H.

Figure 3:
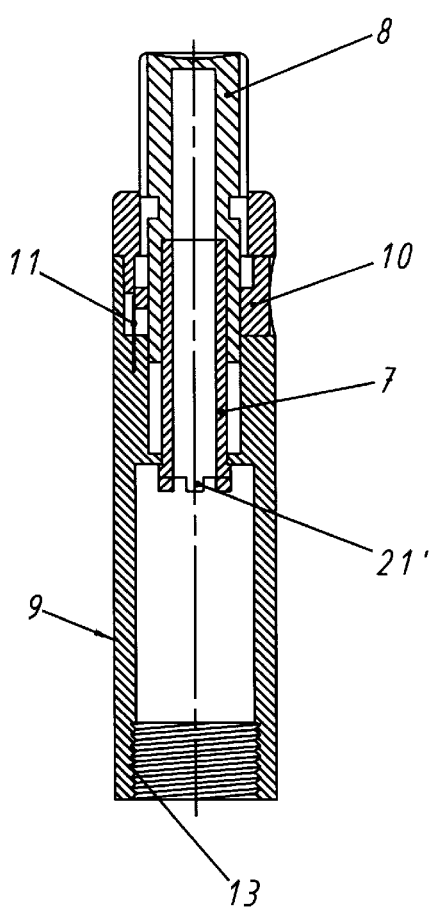
FIG. 3 shows a longitudinal section through the upper part of a device according to FIG. 1.

If the button 8 is pressed down over its entire lift length H, it is held in its final position by the safety device 10 by means of the plate spring 11 as shown in FIG. 3.

Before the patient can turn the button 8 (in order to adjust a new medicament dosage), he must press the safety device 10 at the side of the injection pen so that the spring 6 can push the front plate 17 back, the plunger rod 5, the screw nut 4, the hollow cylinder 7 and the button 8 remaining in their starting positions. Only now is the injection system ready for the adjustment of a new medicament dosage.

What is claimed is:

1. An injection device for injecting a medicament comprising:

a disposable part comprising an ampoule holder for accommodating a container of medicament, said container operably carrying an axially movable plug, a plunger rod operably coupled to the ampoule holder, said plunger rod non-rotatable, but axially movable with respect to the ampoule holder, a nut rotatably and axially fixed with respect to the disposable part during the selecting of dose and a spring disposed around the plunger rod for tending to cause the nut to remain in its axial position; and a reusable part removably connectable to said disposable part and comprising a casing detachably connectable to the ampoule holder, dosing means operably coupled to the casing for selecting a dose of the medicament and comprising a rotatable dosing button and a coupling element for releasably linking the dosing button and the nut and transmitting rotation of the dosing button to the nut, and ejection means operably coupled to the reusable part for moving the plunger rod axially when the disposable part is connected to the reusable part whereby said rod moves said plug to eject the selected dose of medicament from the container.

2. The injection device according to claim 1, wherein said rod has at least two different radii.

3. The injection device according to claim 2, wherein during the operation of said dosing means to select a dose and operation of said ejection means to eject the selected dose, said disposable part and reusable part are not rotated with respect to each other.

4. An injection device with a forward, needle-carrying end and a rear end, said injection device comprising:

A) a disposable part comprising an ampoule holder for accommodating a container containing a liquid medicament and for operably carrying a needle, said container having a cross-sectional area and an axially movable portion having substantially the same cross-sectional area for ejecting the liquid medicament from the container, and a kinematic device operably carried by the disposable part for contacting and axially moving the axially movable portion forward a selected distance; and B) a reusable part connectable to the disposable part and comprising a casing detachably connectable to the ampoule holder of the disposable part, a rotatable dosing button operably coupled to the casing for rotation with respect thereto for selecting the selected distance and for axial movement with respect thereto for injecting a dose of the medicament, and a coupling element releaseably linking the dosing button and the kinematic device and transmitting the rotation of the dosing button to the kinematic device.

5. The injection device according to claim 4, wherein said kinematic device comprises a plunger rod operably carried by the disposable part, said plunger rod non-rotatable, but axially movable, an external screw thread provided on the plunger rod, and a nut with an internal screw thread complementary to the external thread, said nut rotatable, but axially fixed relative to the disposable part during the selecting of the selected distance.

6. The injection device according to claim 5, wherein the plunger rod and nut each have a generally central axis and are generally coaxial.

7. The injection device according to claim 6, wherein the disposable part additionally comprises a spring disposed around the plunger rod and urging the nut toward the rear end of the device when the reusable and disposable parts are connected.

8. The injection device according to claim 7, wherein the selected dose is a function of the cross-sectional area of the container and the selected distance.

* * * * *